(12) United States Patent
Ha

(10) Patent No.: US 10,869,781 B2
(45) Date of Patent: Dec. 22, 2020

(54) OPHTHALMIC TREATMENT APPARATUS AND METHOD FOR CONTROLLING SAME

(71) Applicant: LUTRONIC CORPORATION, Goyang (KR)

(72) Inventor: Tae Ho Ha, Goyang (KR)

(73) Assignee: LUTRONIC CORPORATION, Goyang (KR)

( * ) Notice: Subject to any disclaimer, the term of this patent is extended or adjusted under 35 U.S.C. 154(b) by 190 days.

(21) Appl. No.: 15/756,549

(22) PCT Filed: Aug. 31, 2016

(86) PCT No.: PCT/KR2016/009715
§ 371 (c)(1),
(2) Date: Feb. 28, 2018

(87) PCT Pub. No.: WO2017/039312
PCT Pub. Date: Mar. 9, 2017

(65) Prior Publication Data
US 2018/0243129 A1    Aug. 30, 2018

(30) Foreign Application Priority Data
Aug. 31, 2015  (KR) .......................... 10-2015-0122643

(51) Int. Cl.
*A61F 9/008* (2006.01)
*A61B 3/107* (2006.01)
*A61B 3/12* (2006.01)

(52) U.S. Cl.
CPC .............. *A61F 9/008* (2013.01); *A61B 3/107* (2013.01); *A61B 3/12* (2013.01);
(Continued)

(58) Field of Classification Search
CPC . A61F 9/008; A61F 2009/00863; A61B 3/107
(Continued)

(56) References Cited

U.S. PATENT DOCUMENTS

2006/0100677 A1* 5/2006 Blumenkranz ......... A61F 9/008
607/89
2007/0129775 A1* 6/2007 Mordaunt ............... A61F 9/008
607/88
(Continued)

FOREIGN PATENT DOCUMENTS

JP        2006-524515 A    11/2006
KR    10-2013-0035825 A     4/2013
(Continued)

OTHER PUBLICATIONS

International Search Report for PCT/KR2016/009715 filed on Aug. 31, 2016.

*Primary Examiner* — Gary Jackson
*Assistant Examiner* — Anant A Gupta

(57) ABSTRACT

The present invention relates to an ophthalmic treatment apparatus and a method for controlling same. The ophthalmic treatment apparatus according to the present invention comprises: an image unit for generating an image of the retina area of an eyeball in a horizontal direction with respect to the plane of the focal spot of a therapeutic beam directed by a beam delivery unit; a pattern unit for providing a grid pattern to the retina area so as to correspond to the curvature of the retina area generated by the image unit; and a control unit for controlling the operation of a beam generation unit and the beam delivery unit to radiate the therapeutic beam to the intersection points of the grid pattern on the basis of the grid pattern provided by the pattern unit.

12 Claims, 6 Drawing Sheets

(52) U.S. Cl.
CPC ........... *A61F 2009/00851* (2013.01); *A61F 2009/00863* (2013.01); *A61F 2009/00882* (2013.01)

(58) Field of Classification Search
USPC .......................................................... 606/4
See application file for complete search history.

(56) References Cited

U.S. PATENT DOCUMENTS

| | | |
|---|---|---|
| 2008/0089480 A1 | 4/2008 | Gertner |
| 2013/0116672 A1* | 5/2013 | Yee ................... A61F 9/00821 606/4 |
| 2013/0317487 A1* | 11/2013 | Luttrull ............. A61F 9/00821 606/5 |
| 2014/0243936 A1* | 8/2014 | Ha ..................... A61N 5/0613 607/90 |
| 2015/0202457 A1 | 7/2015 | Ha et al. |
| 2016/0278979 A1 | 9/2016 | Jeong |

FOREIGN PATENT DOCUMENTS

| | | | |
|---|---|---|---|
| KR | 10-2014-0009842 A | 1/2014 | |
| KR | 10-2014-0061001 A | 5/2014 | |
| KR | 10-1472342 B1 | 12/2014 | |
| WO | WO-2014011012 A1 * | 1/2014 | ............. A61F 9/008 |

* cited by examiner

OPHTHALMIC TREATMENT APPARATUS AND METHOD FOR CONTROLLING SAME

CROSS-REFERENCE TO RELATED APPLICATIONS

The present specification is a U.S. National Stage of International Patent Application No. PCT/KR2016/009715 filed Aug. 31, 2016, which claims priority to and the benefit of Korean Patent Application No. 10-2015-0122643 filed in the Korean Intellectual Property Office on Aug. 31, 2015, the entire contents of which are incorporated herein by reference.

TECHNICAL FIELD

The present invention relates to an ophthalmic treatment apparatus and a method of controlling the same, and more particularly, to an ophthalmic treatment apparatus and a method of controlling the same that irradiate a lesion generated in the eyeball with a therapeutic beam.

BACKGROUND ART

In recent years, medical treatment devices using various optical characteristics such as laser beams have been applied to various medical fields such as surgery, dermatology, ophthalmology, and the like, and their utilization rate is on the rise. Particularly, in the aforementioned medical fields, the ophthalmic treatment apparatus specialized in ophthalmology uses a laser beam of a certain wavelength band as a therapeutic beam.

Here, the ophthalmic treatment apparatus is used for treating various ocular diseases such as glaucoma, cataract, and macular degeneration by irradiating a laser beam with a certain wavelength band onto the eyeball. Of course, the ophthalmic treatment apparatus may irradiate laser beams with different wavelength bands or perform different modes in irradiation of the laser beam for the purpose of treating various lesions such as glaucoma, cataract, and macular degeneration.

Meanwhile, a conventional treatment apparatus entitled "Selective laser targeting of pigmented ocular cells" is disclosed in the publication of U.S. Pat. No. 5,549,596. The above-stated related art document discloses a technique capable of shortening a treatment time by irradiating a patient's lesion with a plurality of lasers in a pattern of a certain area.

However, the treatment apparatus disclosed in the related art document irradiates a plurality of spots like a pattern with the same laser in order to shorten the treatment time. However, such a plurality of spots are irradiated onto a plane of the same focal spot, so there is a problem that errors may occur in a lesion area having a curvature like a retina.

DISCLOSURE

Technical Problem

An object of the present invention is to provide an ophthalmic treatment apparatus and a method of controlling the same that improve an irradiation structure and an irradiation method so that a therapeutic beam can be irradiated along a curvature with respect to a treatment region of the eyeball having its own curvature.

Further, it is another object of the present invention to provide an ophthalmic treatment apparatus and a method of controlling the same improve an irradiation structure and an irradiation method so that the position of the therapeutic beam irradiated to the treatment region of the eyeball can be measured.

Technical Solution

The object according to the present invention is achieved by providing an ophthalmic treatment apparatus having a beam generation unit for generating a therapeutic beam and a beam delivery unit for guiding the therapeutic beam into the eyeball, the ophthalmic treatment apparatus including: an image unit for generating an image of a retina region of the eyeball in the lateral direction with respect to a plane of a focal spot of the therapeutic beam guided by the beam delivery unit; a pattern unit for providing a grid pattern to the retina region corresponding to a curvature of the retina region generated by the image unit; and a control unit for controlling operation of the beam generation unit and the beam delivery unit to irradiate intersecting points of the grid pattern with the therapeutic beam based on the grid pattern provided by the pattern unit.

Here, the plane of the focal spot may include: a first plane forming a tangent plane at an arc of the retina region through which an optical axis of the therapeutic beam passes; and a second plane which is parallel to the first plane along the optical axis and connects both sides of an arc while interposing a point of contact of the retina region therebetween.

The ophthalmic treatment apparatus may further include a curvature calculation unit for calculating the curvature of the retina region according to a distance between the first plane and the second plane.

It is preferable that the pattern unit provides the grid pattern having a curvature corresponding to the curvature of the retina region calculated by the curvature calculation unit to the retina region.

More preferably, the pattern unit may overlap the grid pattern on a lesion generated in the retina region.

Also, the control unit may control the operation of the beam generation unit and the beam delivery unit to irradiate the intersecting points of the grid pattern overlapped on the lesion with the therapeutic beam.

The pattern unit may provide a plurality of grid patterns on the lesion such that partial areas of the plurality of grid patterns overlap one another.

After the therapeutic beam is irradiated onto the intersecting points of any one among the plurality of grid patterns provided on the lesion, the pattern unit may provide another one of the grid patterns on the lesion such that a partial area of any one of the grid patterns mutually overlaps with another one of the grid patterns.

When another one of the grid patterns is provided on the lesion, the control unit may control the operation of the beam generation unit and the beam delivery unit to irradiate the intersecting points of another one of the grid patterns with the therapeutic beam except the intersecting points where any one of grid patterns and another one of grid patterns mutually overlap each other.

Also, the object according to the present invention is also achieved by providing an ophthalmic treatment apparatus having a beam generation unit for generating a therapeutic beam and a beam delivery unit for guiding the therapeutic beam into the eyeball, the ophthalmic treatment apparatus including: an image unit for generating an image of a lesion formed in a retinal region of the eyeball; a pattern unit for sequentially providing a plurality of grid patterns such that partial areas of the plurality of grid patterns are mutually overlapped on the lesion one another; a control unit for controlling operation of the beam generation unit and the beam delivery unit such that the therapeutic beam is sequentially irradiated onto intersecting points of the plurality of grid patterns provided on the lesion when the plurality of grid patterns are sequentially provided on the lesion.

Here, the control unit may include: when any one among the plurality of grid patterns is provided on the lesion by the pattern unit, a first mode for controlling the operation of the beam generation unit and the beam delivery unit such that the therapeutic beam is irradiated onto the intersecting points of any one of the grid patterns; and when another one among the plurality of grid patterns is provided to be mutually overlapped with a partial area of any one of the grid patterns by the pattern unit after the control unit is controlled in the first mode, a second mode for controlling the operation of the beam generation unit and the beam delivery unit such that the therapeutic beam is irradiated onto the intersecting points of another one of the grid patterns except the overlapped intersecting points where the any one of grid patterns and another one of the grid patterns mutually overlap each other.

Also, the image unit may include: a first image unit for generating an image of the lesion; and a second image unit for generating an image of the retina region in the lateral direction with respect to a plane of a focal spot of the therapeutic beam guided by the beam delivery unit.

The plane of the focal spot may include: a first plane forming a tangent plane at an arc of the retina region through which an optical axis of the therapeutic beam passes; and a second plane which is parallel to the first plane along the optical axis and connects both sides of an arc formed while interposing a point of contact of the retina region therebetween.

The ophthalmic treatment apparatus may further include a curvature calculation unit for calculating a curvature of the retina region according to a distance between the first plane and the second plane.

Preferably, the pattern unit may provide the plurality of grid patterns having a curvature corresponding to the curvature of the retina region calculated by the curvature calculation unit to the retina region.

Meanwhile, the object according to the present invention is also achieved by providing a method of controlling an ophthalmic treatment apparatus, the method including the steps of: (a) generating an image of a retina region of the eyeball in the lateral direction of a plane of a focal spot onto which a therapeutic beam is irradiated; (b) analyzing a curvature of the image of the generated retina region and providing a grid pattern corresponding to the analyzed curvature of the retina region to the retina region; and (c) irradiating intersecting points of the grid pattern provided in the retina region corresponding to the curvature of the retina region with the therapeutic beam.

Here, it is preferable that the step (b) is providing the grid pattern having a curvature corresponding to the curvature of the image of the retina region to the retina region.

More preferably, the step (b) may be overlapping the grid pattern on a lesion generated in the retina region.

Also, the method of controlling an ophthalmic treatment apparatus may further include (d) providing a plurality of the grid patterns on the lesion to overlap with a partial area of the grid pattern provided in the step (b).

In addition, the method of controlling an ophthalmic treatment apparatus may further include (e) irradiating intersecting points of the grid patterns provided in the step (d) with the therapeutic beam except intersecting points where the grid patterns provided in the steps (b) and (d) mutually overlap one another.

The details of other embodiments are included in the detailed description and the drawings.

Advantageous Effects

Effects of the ophthalmic treatment apparatus and the method of controlling the same according to the present invention are as follows.

First, since the irradiation position of a therapeutic beam can be determined by irradiating the intersecting points of the grid pattern with the therapeutic beam, the time required for treatment can be reduced and the treatment efficiency can be improved.

Second, since errors according to the irradiation positions of the therapeutic beam can be reduced by calculating the curvature of the retinal region to be irradiated with the therapeutic beam and providing the retinal region with a grid pattern having a curvature corresponding to the calculated curvature, the treatment efficiency can be improved.

Third, since when a plurality of grid patterns are sequentially provided to the retina region, the therapeutic beam can be irradiated onto intersecting points except the intersecting points of the grid patterns of the overlapped region, the time required for treatment can be reduced.

MODE FOR INVENTION

Hereinafter, an ophthalmic treatment apparatus and a method of controlling the same according to an embodiment of the present invention will be described in detail with reference to the accompanying drawings.

Prior to the description of the present invention, it is to be noted in advance that the grid pattern used in the ophthalmic treatment apparatus according to an embodiment of the present invention is shown and specified in the form of a square, but other polygonal shapes other than a square shape can also be used.

Figure 1:
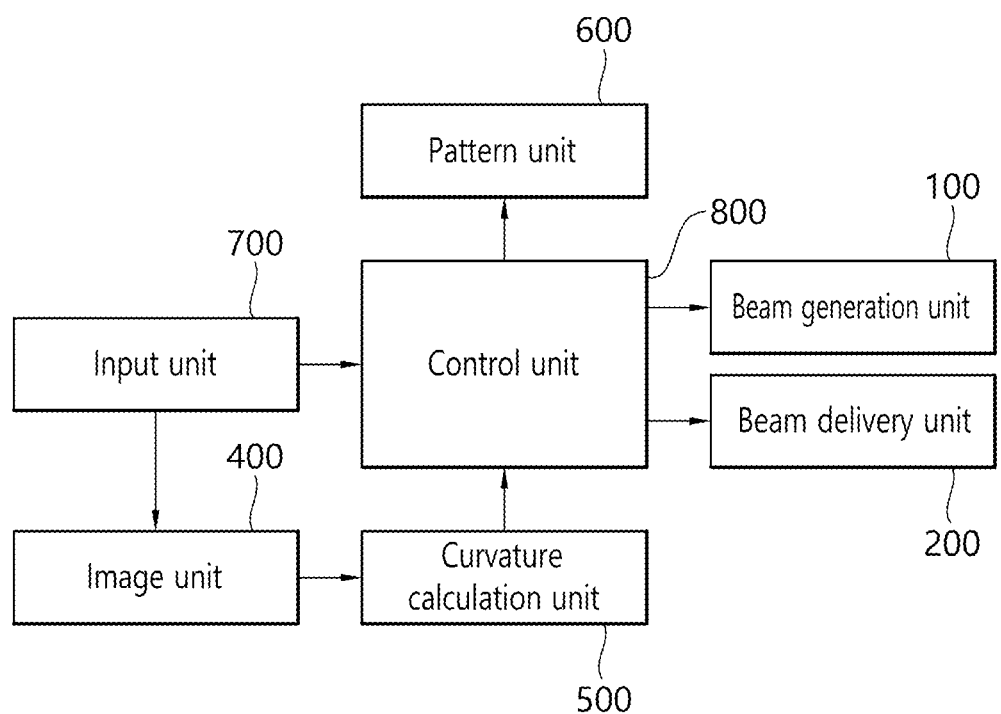
FIG. 1 is a control block diagram of an ophthalmic treatment apparatus according to an embodiment of the present invention.
Figure 2:
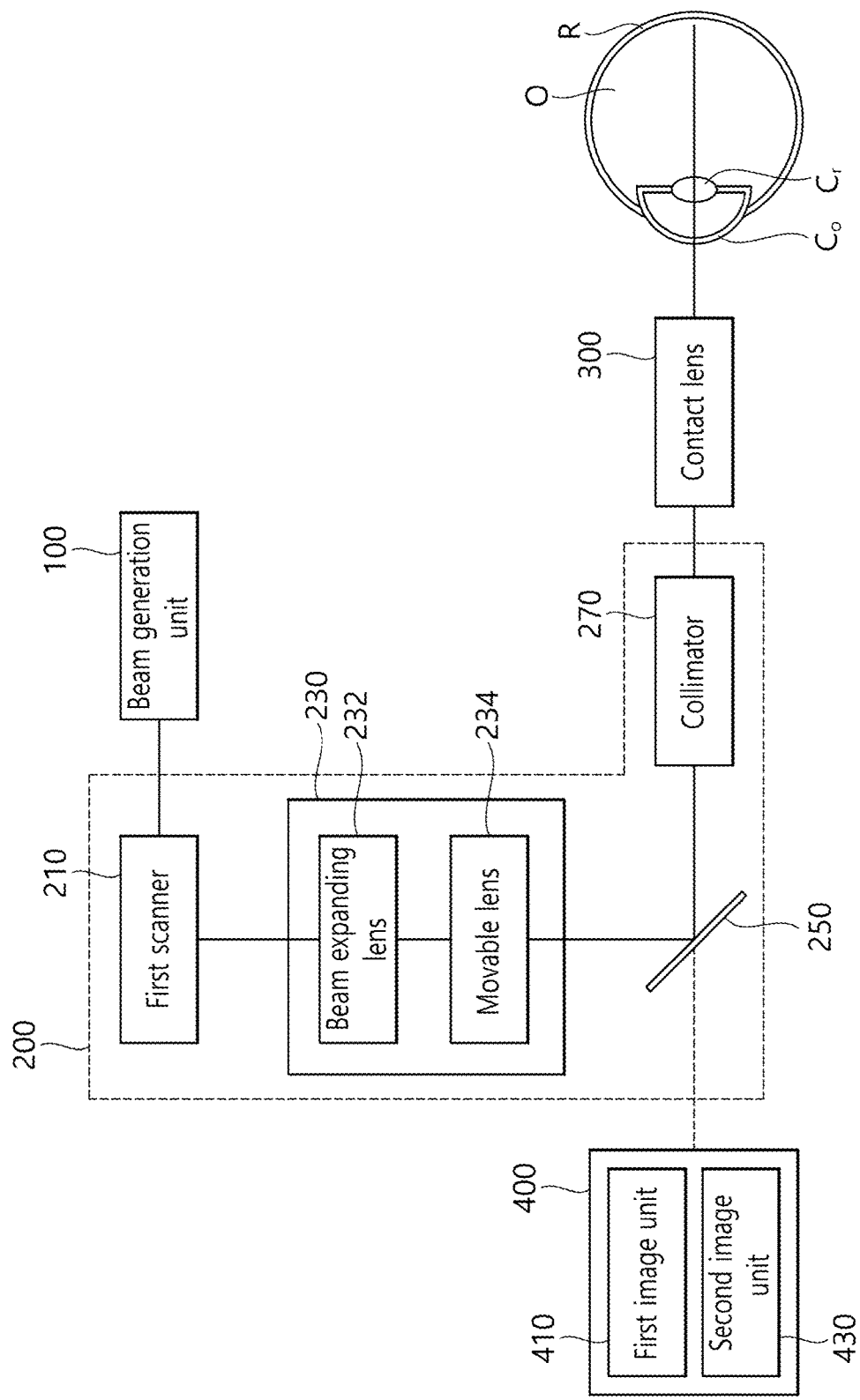
FIG. 2 is a schematic configuration diagram of the ophthalmic treatment apparatus according to the embodiment of the present invention.

FIG. 1 is a control block diagram of an ophthalmic treatment apparatus according to an embodiment of the present invention, and FIG. 2 is a schematic configuration diagram of the ophthalmic treatment apparatus according to the embodiment of the present invention.

As shown in FIGS. 1 and 2, the ophthalmic treatment apparatus 10 according to the embodiment of the present invention includes a beam generation unit 100, a beam delivery unit 200, an image unit 400, a pattern unit 600, and a control unit 800. Also, the ophthalmic treatment apparatus 10 according to the embodiment of the present invention further includes a contact lens 300, a curvature calculation unit 500, and an input unit 700. Here, the ophthalmic treatment apparatus 10 according to the embodiment of the present invention is used for treating a retinal (R) region in consideration of a curvature of the eyeball O. The ophthalmic treatment apparatus according to the embodiment of the present invention is configured such that allow a therapeutic beam passed through the cornea Co and the crystalline lens Cr of the eyeball is irradiated onto the retina R.

The beam generation unit 100 generates a therapeutic beam based on an input signal received from the input unit 700 to be described later. The beam generation unit 100 according to the embodiment of the present invention includes a laser diode that generates a laser beam so that the laser beam can be used as a therapeutic beam. Here, the therapeutic beam generated by the beam generation unit 100 may vary depending on the type of light source (not shown).

The therapeutic beam generated from the beam generation unit 100 has a wavelength band capable of treating a lesion (not shown) of the eyeball O. As one embodiment of the present invention, the therapeutic beam generated from the beam generation unit 100 may have a wavelength band of 532 nm to 1064 nm. However, the therapeutic beam generated from the beam generation unit 100 may have a wavelength band of less than 532 nm or more than 1064 nm, depending on the treatment purpose or the lesion to be treated, other than the above-mentioned wavelength band of 532 nm to 1064 nm.

The beam delivery unit 200 guides the therapeutic beam generated from the beam generation unit 100 to the eyeball. Specifically, the beam delivery unit 200 guides the therapeutic beam to the lesion formed in the eyeball O by control of the control unit 800. Specifically, the beam delivery unit 200 guides the therapeutic beam generated from the beam generation unit 100 to the retina R region of the eyeball O. The beam delivery unit 200 of the present invention includes a first scanner 210, a second scanner 230, a beam splitter 250, and a collimator 270.

The first scanner 210 guides the therapeutic beam provided from the beam generation unit 100 onto a plane F (see FIG. 3) of a focal spot to be described later. That is, assuming that a XY plane, which is in the lateral direction of an optical axis OA (see FIG. 3) of the therapeutic beam, is referred to as a plane F of the focal spot, the first scanner 210 adjusts an irradiation position of the therapeutic beam on the plane F of the focal spot.

The second scanner 230 adjusts a position of the focal spot along the optical axis OA, and more specifically a position of the focal spot of the therapeutic beam incident from the first scanner 210 along the optical axis OA. That is, the second scanner 230 adjusts a position of the focal spot of the therapeutic beam along a Z axis, which is in the lateral direction of the XY plane. If explained in detail, the first scanner 210 adjusts the position of the focal spot on the XY plane, and the second scanner 230 adjusts the position of the focal spot in the depth direction that is the Z axis direction. The second scanner 230 adjust the position of the focal spot of the therapeutic beam in the Z axis direction corresponding to a curvature of the grid pattern G (see FIGS. 4 and 5) provided from the pattern unit 600 to be described later, that is, corresponding to the curvature of the retina R region. The second scanner 230 of the present invention includes a beam expanding lens 232 and a movable lens 234.

The beam expanding lens 232 expands the therapeutic beam incident from the first scanner 210. The movable lens 234 moves relative to the beam expanding lens 232 such that the therapeutic beam passed through the beam expanding lens 232 is irradiated along the curvature of the retinal R region. The movable lens 234 is moved relative to the beam expanding lens 232, so that the therapeutic beam is irradiated while being adjusted along the Z axis.

The beam splitter 250 guides the therapeutic beam provided from the first scanner 210 and the second scanner 230 to the contact lens 300. Specifically, the beam splitter 250 guides the therapeutic beam to the collimator 270. The collimator 270 guides the therapeutic beam provided from the beam splitter 250 to the contact lens 300. An objective lens is use in the collimator 270.

The contact lens 300 is placed on the front surface of the eyeball O by the operator such that the contact lens 300 is in contact with the eyeball in order to secure the visibility of the retina R region. That is, the contact lens 300 is used so that the operator can see the retina R. The contact lens 300 is grasped by the operator and disposed between the eyeball O and the collimator 270 of the above-described beam delivery unit 200.

Figure 3:
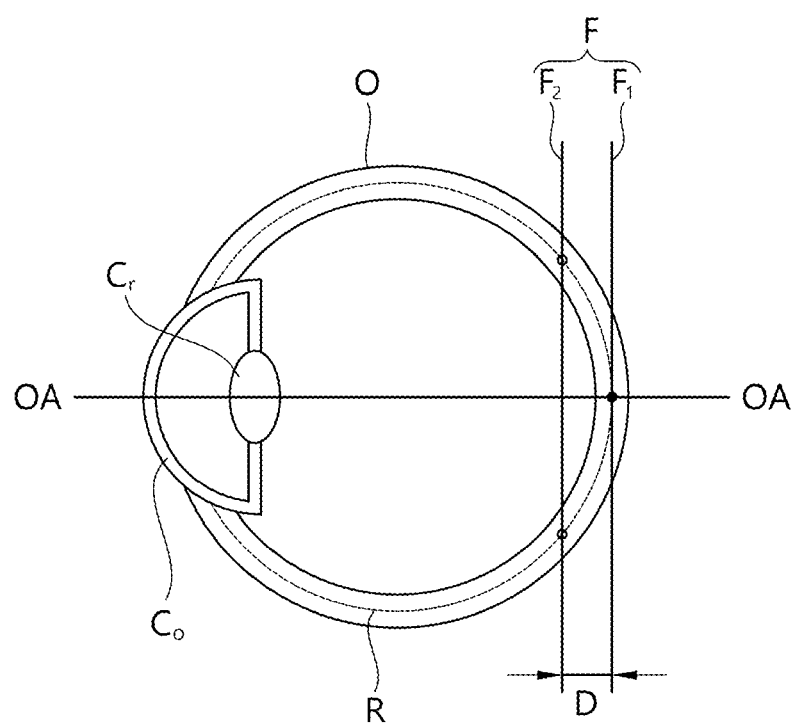
FIG. 3 is a schematic view of a plane of a focal spot formed on the retina of the eyeball according to the embodiment of the present invention.
Figure 4:
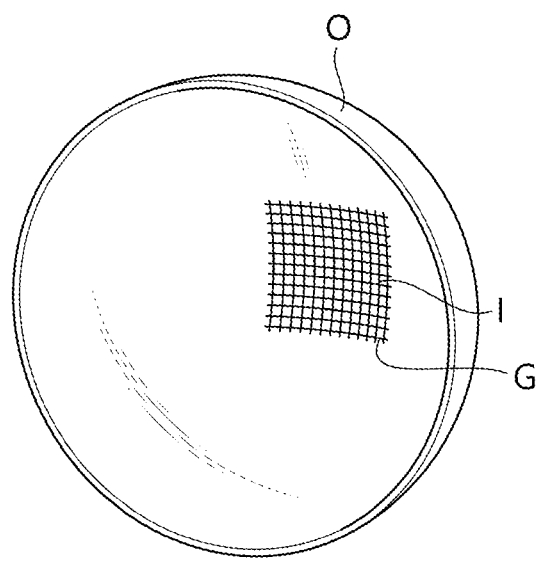
FIG. 4 is a schematic perspective view in which a grid pattern is provided by the ophthalmic treatment apparatus according to the embodiment of the present invention.
Figure 5:
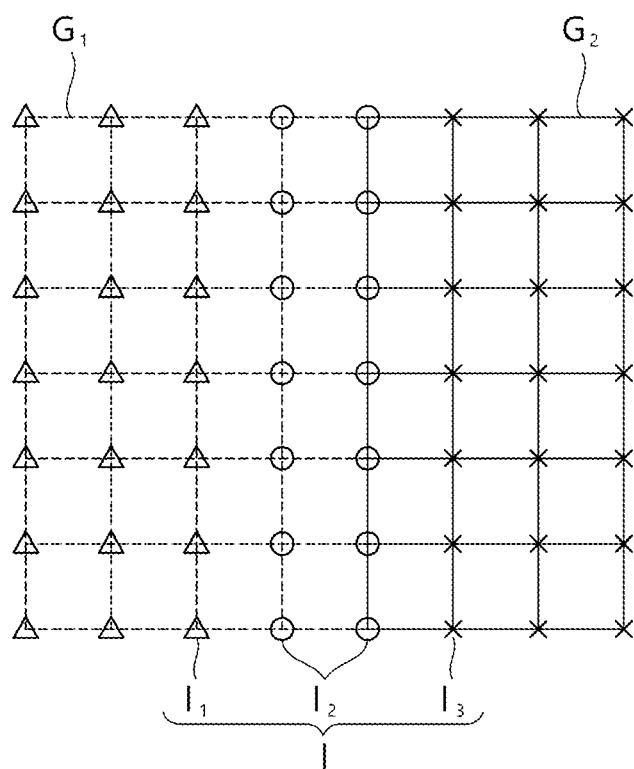
FIG. 5 is a schematic configurational diagram for irradiating a therapeutic beam onto grid patterns provided by the ophthalmic treatment apparatus according to the embodiment of the present invention.

Next, FIG. 3 is a schematic view of a plane of a focal spot formed on the retina of the eyeball according to the embodiment of the present invention, FIG. 4 is a schematic perspective view in which a grid pattern is provided by the ophthalmic treatment apparatus according to the embodiment of the present invention, and FIG. 5 is a schematic configurational diagram for irradiating a therapeutic beam onto grid patterns provided by the ophthalmic treatment apparatus according to the embodiment of the present invention.

As shown in FIGS. 3 to 5, the image unit 400 generates an image of the retina R region of the eyeball O in the lateral direction with respect to the plane F of the focal spot of the therapeutic beam guided by the beam delivery unit 200. The image unit 400 is provided for performing a tomography of the eyeball O, for example, OCT (Optical Coherence Tomography) or the like may be used. Further, the image unit 400 photographs a lesion formed in the retina R region together with tomography of the eyeball (O). Specifically, the image unit 400 includes a first image unit 410 and a second image unit 430. The first image unit 410 generates an image of the lesion formed in the retina R region. The second image unit 430 generates an image of the retina R region in the lateral direction with respect to the plane of the focal spot of the therapeutic beam guided by the beam delivery unit 200.

Here, the plane F of the focal spot taken by the image unit 400 includes a first plane $F_1$ forming a tangent plane at an arc of the retina R region through which the optical axis OA of the therapeutic beam passes, and a second plane $F_2$ which is parallel to the first plane $F_1$ along the optical axis and connects both sides of an arc formed while interposing a point of contact of the retina R region therebetween.

The curvature calculation unit 500 calculates the curvature of the retina region by the image unit. The curvature calculation unit 500 calculates the curvature of the retina R region by using a separation distance D between the first plane $F_1$ and the second plane $F_2$ taken by the image unit 400. The method of calculating the curvature by the curvature calculation unit 500 will be omitted because the method can be performed by various methods which are mathematically well known. Further, the curvature calculation unit 500 may calculate the curvature by analyzing an image by tomography of the eyeball O other than the curvature calculating method using the separation distance (D).

The pattern unit 600 provides a grid pattern G to the retina R region corresponding to the curvature of the retina R region generated by the image unit 400. Specifically, the pattern unit 600 provides a grid pattern G having a curvature corresponding to the curvature of the retinal R region calculated by the curvature calculation unit 500 to the retinal region. As such, the pattern unit 600 provides the grid pattern G having the curvature corresponding to the curvature of the retina R region, thereby improving the treatment efficiency according to the reduction in the irradiation errors of the therapeutic beam.

The pattern unit 600 overlaps the grid pattern G on the lesion generated in the retina R region. The pattern unit 600 provides a plurality of grid patterns G on the retina R region. Specifically, the pattern unit 600 sequentially provides a plurality of grid patterns G to the retina R region. That is, the pattern unit 600 provides any one of the grid patterns G to the retina R region, and then after the therapeutic beam is irradiated onto any one of intersecting points I of the provided grid pattern, and irradiates another one of grid patterns G to the retinal (R) region. At this time, the pattern unit 600 sequentially provides the grid patterns G so that partial areas of the plurality of grid patterns G overlap one another. Specifically, as shown in FIG. 5, after the pattern unit 600 provides a first grid pattern $G_1$, it provides a second grid pattern $G_2$ so that the second grid pattern $G_2$ and the first grid pattern $G_1$ have overlapped intersecting points $I_2$.

The input unit 700 transmits an input signal to the beam generation unit 100 so that the therapeutic beam is generated. Also, the input unit 700 transmits an input signal to the image unit 400 so that an image of the retina R region of the eyeball O is taken and generated from the image unit 400.

Finally, the control unit 800 controls operation of the beam generation unit 100 and the beam delivery unit 200 to irradiate intersecting points I of the grid pattern G with the therapeutic beam based on the grid pattern G provided in the pattern unit 600. Also, the control unit 800 controls the operation of the beam generation unit 100 and the beam delivery unit 200 in such a way that after any one among the plurality of grid patterns G is provided on the retinal R region and the therapeutic beam is irradiated onto intersecting points I of the provided grid pattern G, and then when another one of grid patterns G is provided on the lesion I, the therapeutic beam is irradiated onto intersecting points I of another of the grid patterns G except intersecting points I where any one of grid patterns G and another one of grid patterns G overlap each other.

If explained in more detail, when the first grid pattern $G_1$ among the plurality of grid patterns G is provided on the lesion by the pattern unit 600, the control unit 800 is operated in a first mode for controlling the operation of the beam generation unit 100 and the beam delivery unit 200 such that the therapeutic beam is irradiated onto the first intersecting points $I_1$ and the overlapped intersecting points $I_2$ of the first grid pattern (Here, the first intersecting points and the overlapped intersecting points are the entire intersecting points of the first grid pattern). Meanwhile, when the second grid pattern $G_2$ among the plurality of grid patterns G is provided to be mutually overlapped with a partial area of the first grid pattern $G_1$ by the pattern unit 600 after the control unit 800 is controlled in the first mode, the control unit 800 is operated in a second mode for controlling the operation of the beam generation unit 100 and the beam delivery unit 200 such that the therapeutic beam is irradiated onto second intersecting points $I_3$ of the second grid pattern $G_2$ except the overlapped intersecting points I where the first grid pattern $G_1$ and the second grid pattern $G_2$ mutually overlap each other.

Figure 6:
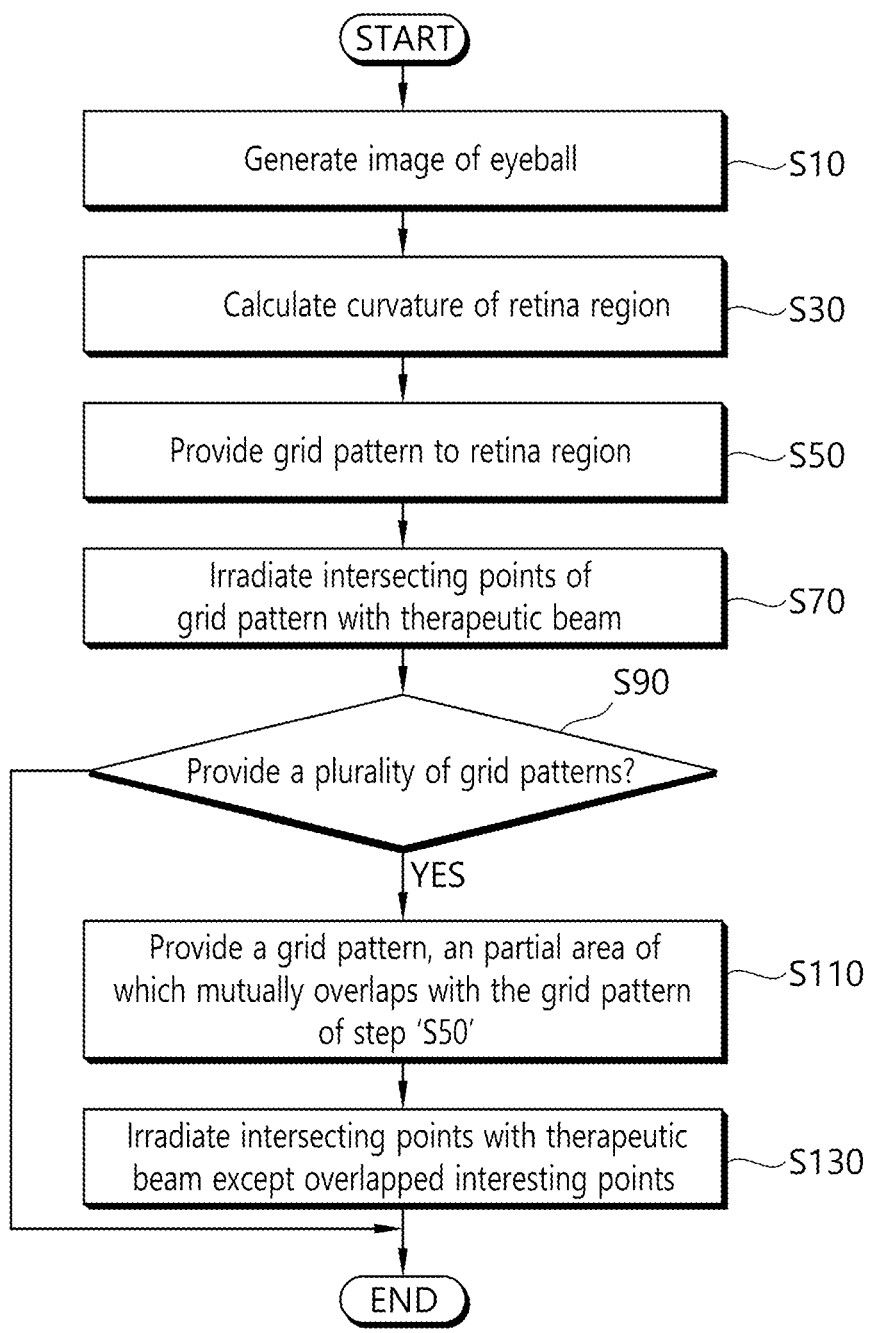
FIG. 6 is a control flowchart of the ophthalmic treatment apparatus according to the embodiment of the present invention.

FIG. 6 is a control flowchart of the ophthalmic treatment apparatus according to the embodiment of the present invention.

The operation of the ophthalmic treatment apparatus 10 according to the embodiment of the present invention with the above structure is as follows.

First, an image of the eyeball O is generated (S10). A tomographic image of the eyeball O and a lesion image of a retina R region are generated by using an image unit 400. At this time, the image unit 400 generates the image of the eyeball O in the lateral direction of a plane F of a focal spot. A curvature of the retina R region is calculated by using the image generated by the image unit 400 (S30).

Next, a grid pattern G having a curvature corresponding to the curvature of the retina R region is provided on the retina R region (S50). Then, a therapeutic beam is irradiated onto intersecting points I of the grid pattern G (S70). Specifically, a first grid pattern $G_1$ is provided in the retina R region and the therapeutic beam is irradiated onto first intersecting points $I_1$ and overlapped intersecting points $I_2$.

It is determined whether or not a plurality of grid patterns G are to be provided (S90). If it is determined in step S90 that the plurality of grid patterns G are to be provided, a second grid pattern G2 is provided such that a partial area of the second grid pattern G2 mutually overlaps with the first grid pattern G1 provided in step S50 (S110). The therapeutic beam is irradiated onto second intersecting points 13 of the second grid pattern G2 except the overlapped intersecting points I where the first grid pattern G1 and the second grid pattern G2 overlap each other (S130). On the other hand, if it is not necessary to provide additional grid pattern G in step S90, the process ends.

Accordingly, since the irradiation position of a therapeutic beam can be determined by irradiating the intersecting points of the grid pattern with the therapeutic beam, the time required for treatment can be reduced and the treatment efficiency can be improved.

In addition, since errors according to the irradiation positions of the therapeutic beam can be reduced by calculating the curvature of the retinal region to be irradiated with the therapeutic beam and providing the retinal region with a grid pattern having a curvature corresponding to the calculated curvature, the treatment efficiency can be improved.

In addition, since when a plurality of grid patterns are sequentially provided to the retina region, the therapeutic beam can be irradiated onto intersecting points except the intersecting points of the grid patterns of the overlapped region, the time required for treatment can be reduced.

While the embodiments of the present invention have been described with reference to the accompanying drawings, it will be understood by a person with ordinary skill in the art that the present invention may be embodied in many other specific forms without departing from the technical spirit or essential features of the present invention. Therefore, it is to be understood that the above-described embodiments are illustrative in all aspects and not restrictive. The scope of the present invention is defined by the claims to be described rather than the detailed description, and all changes or modifications derived from the meaning and scope of the claims and their equivalents are to be construed as being included within the scope of the present invention.

The invention claimed is:

1. An ophthalmic treatment apparatus, comprising:
a beam generation unit for generating a therapeutic beam;
a beam delivery unit for guiding the therapeutic beam into an eyeball;
an image unit for generating an image of a retina region of the eyeball in a lateral direction with respect to a plane of a focal spot of the therapeutic beam guided by the beam delivery unit; and
a control unit for controlling the beam generation unit and the beam delivery unit to irradiate intersecting points of a grid pattern with the therapeutic beam based on the grid pattern being provided to the retina region corresponding to a curvature of the retina region generated by the image unit,
wherein a plurality of grid patterns are provided on a lesion generated in the retina region such that the plurality of grid patterns partially overlap each other,
wherein, after the therapeutic beam is irradiated onto intersecting points of one of the plurality of grid patterns provided on the lesion, another one of the plurality of grid patterns is provided on the lesion such that the one of the plurality of grid patterns partially overlaps the other one of the plurality of grid patterns, and
wherein, when the other one of the plurality of grid patterns is provided on the lesion, the control unit controls the beam generation unit and the beam delivery unit to irradiate intersecting points of the other one of the plurality of grid patterns with the therapeutic beam except intersecting points where the one of the plurality of grid patterns overlaps the other one of the plurality of grid patterns.

2. The apparatus according to claim 1, wherein the plane of the focal spot comprises:
a first plane forming a tangent plane at an arc of the retina region through which an optical axis of the therapeutic beam passes; and
a second plane which is parallel to the first plane along the optical axis and connects both sides of an arc while interposing a point of contact of the retina region therebetween.

3. The apparatus according to claim 2, further comprising a curvature calculation unit for calculating the curvature of the retina region according to a distance between the first plane and the second plane.

4. The apparatus according to claim 3, wherein the grid pattern has a curvature corresponding to the curvature of the retina region calculated by the curvature calculation unit and is provided to the retina region.

5. The apparatus according to claim 1, wherein the grid pattern overlaps on the lesion generated in the retina region.

6. The apparatus according to claim 5, wherein the control unit controls the beam generation unit and the beam delivery unit to irradiate the intersecting points of the grid pattern overlapped on the lesion with the therapeutic beam.

7. An ophthalmic treatment apparatus, comprising:
a beam generation unit for generating a therapeutic beam;
a beam delivery unit for guiding the therapeutic beam into an eyeball;
an image unit for generating an image of a lesion formed in a retinal region of the eyeball; and
a control unit for controlling the beam generation unit and the beam delivery unit such that the therapeutic beam is sequentially irradiated onto intersecting points of a plurality of grid patterns provided on the lesion when the plurality of grid patterns are sequentially provided on the lesion such that that the plurality of grid patterns partially overlap each other on the lesion,
wherein the control unit comprises:
when one of the plurality of grid patterns is provided on the lesion, a first mode for controlling the beam generation unit and the beam delivery unit such that the therapeutic beam is irradiated onto intersecting points of the one of the plurality of grid patterns; and
when another one of the plurality of grid patterns is provided to partially overlap the one of the plurality of grid patterns after the control unit is controlled in the first mode, a second mode for controlling the beam generation unit and the beam delivery unit such that the therapeutic beam is irradiated onto intersecting points of the other one of the plurality of grid patterns except intersecting points where the one of the plurality of grid patterns overlaps the other one of the plurality of grid patterns.

8. The apparatus according to claim 7, wherein the image unit comprises:
a first image unit for generating an image of the lesion; and
a second image unit for generating an image of the retina region in a lateral direction with respect to a plane of a focal spot of the therapeutic beam guided by the beam delivery unit.

9. The apparatus according to claim 8, wherein the plane of the focal spot comprises:
a first plane forming a tangent plane at an arc of the retina region through which an optical axis of the therapeutic beam passes; and
a second plane which is parallel to the first plane along the optical axis and connects both sides of an arc formed while interposing a point of contact of the retina region therebetween.

10. The apparatus according to claim 9, further comprising a curvature calculation unit for calculating a curvature of the retina region according to a distance between the first plane and the second plane.

11. The apparatus according to claim 10, wherein the plurality of grid patterns have a curvature corresponding to the curvature of the retina region calculated by the curvature calculation unit and are provided to the retina region.

12. A method of controlling an ophthalmic treatment apparatus, the method comprising:
generating an image of a retina region of an eyeball in a lateral direction of a plane of a focal spot onto which a therapeutic beam is irradiated;
analyzing a curvature of the image of the retina region;
providing a grid pattern corresponding to the analyzed curvature of the retina region to the retina region; and
irradiating intersecting points of the grid pattern provided in the retina region corresponding to the curvature of the retina region with the therapeutic beam,
wherein the providing comprises sequentially providing a plurality of grid patterns on a lesion formed in the retina region to partially overlap each other; and
wherein the irradiating comprises irradiating intersecting points of the plurality of grid patterns with the therapeutic beam except intersecting points where the plurality of grid patterns overlap each other.

* * * * *